(12) United States Patent
Zhang

(10) Patent No.: US 10,803,279 B2
(45) Date of Patent: Oct. 13, 2020

(54) PHOTOSENSITIVE COMPONENT, DISPLAY DEVICE AND FINGERPRINT IDENTIFICATION METHOD

(71) Applicants: BOE TECHNOLOGY GROUP CO., LTD., Beijing (CN); ORDOS YUANSHENG OPTOELECTRONICS CO., LTD., Inner Mongolia (CN)

(72) Inventor: Hao Zhang, Beijing (CN)

(73) Assignees: BOE TECHNOLOGY GROUP CO., LTD., Beijing (CN); ORDOS YUANSHENG OPTOELECTRONICS CO., LTD., Ordos, Inner Mongolia (CN)

( * ) Notice: Subject to any disclaimer, the term of this patent is extended or adjusted under 35 U.S.C. 154(b) by 132 days.

(21) Appl. No.: 16/163,670

(22) Filed: Oct. 18, 2018

(65) Prior Publication Data

US 2019/0122019 A1    Apr. 25, 2019

(30) Foreign Application Priority Data

Oct. 24, 2017 (CN) .......................... 2017 1 1000631

(51) Int. Cl.
*A61B 5/1172* (2016.01)
*G06K 9/00* (2006.01)
*G06F 3/042* (2006.01)

(52) U.S. Cl.
CPC .......... *G06K 9/0002* (2013.01); *A61B 5/1172* (2013.01); *G06F 3/0421* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,400,662 A | * | 3/1995 | Tamori | ................. G06K 9/0002 73/862.046 |
| 8,497,507 B2 | * | 7/2013 | Yang | ..................... H01L 29/458 257/59 |

(Continued)

FOREIGN PATENT DOCUMENTS

| | | |
|---|---|---|
| CN | 102017147 A | 4/2011 |
| CN | 104137287 A | 11/2014 |

(Continued)

OTHER PUBLICATIONS

First Office Action for Chinese Application No. 201711000631.3, dated Aug. 28, 2019, 10 pages.

*Primary Examiner* — Omar S Ismail
(74) *Attorney, Agent, or Firm* — Brooks Kushman P.C.

(57) ABSTRACT

The present application discloses a photosensitive component, a display device and a fingerprint identification method. The photosensitive component comprises a first electrode layer, a first photosensitive material layer arranged on the first electrode layer, a second electrode layer arranged on the first photosensitive material layer, a second photosensitive material layer arranged on the second electrode layer, and a third electrode layer arranged on the second photosensitive material layer. The first electrode layer is made of an opaque material, and the third electrode layer is made of a transparent material.

14 Claims, 2 Drawing Sheets

(56) References Cited

U.S. PATENT DOCUMENTS

| | | | |
|---|---|---|---|
| 9,006,637 B2* | 4/2015 | Deleniv | H01L 31/09 250/214 R |
| 2004/0252867 A1* | 12/2004 | Lan | G06K 9/0004 382/124 |
| 2007/0262244 A1 | 11/2007 | Padinger et al. | |
| 2008/0179762 A1* | 7/2008 | Cho | H01L 29/66833 136/252 |
| 2009/0152664 A1* | 6/2009 | Klem | H01L 27/14641 257/440 |
| 2012/0090685 A1* | 4/2012 | Forrest | H01L 51/0012 136/263 |
| 2015/0010265 A1* | 1/2015 | Popovich | G06K 9/0004 385/10 |
| 2015/0155400 A1* | 6/2015 | Xue | H01L 27/1446 257/53 |
| 2016/0283773 A1* | 9/2016 | Popovich | G06K 9/00046 |
| 2017/0123593 A1* | 5/2017 | Send | G06F 3/0416 |
| 2017/0228529 A1* | 8/2017 | Huang | G06K 9/0002 |
| 2017/0363465 A1* | 12/2017 | Send | G01S 11/12 |
| 2017/0363741 A1* | 12/2017 | Send | H04N 5/2354 |
| 2018/0239943 A1 | 8/2018 | Xu et al. | |
| 2019/0034020 A1* | 1/2019 | He | G06F 3/0416 |

FOREIGN PATENT DOCUMENTS

| | | |
|---|---|---|
| CN | 106326845 A | 1/2017 |
| CN | 207249691 U | 4/2018 |

\* cited by examiner

PHOTOSENSITIVE COMPONENT, DISPLAY DEVICE AND FINGERPRINT IDENTIFICATION METHOD

CROSS-REFERENCE TO RELATED APPLICATION

This application claims priority to Chinese Patent Application No. 201711000631.3 filed on Oct. 24, 2017, which is incorporated herein by reference in its entirety.

TECHNICAL FIELD

The present disclosure relates to the field of display technologies, in particular to a photosensitive component, a display device and a fingerprint identification method.

BACKGROUND

With the development of science and technologies, in the current mobile internet era, various kinds of personal mobile terminal devices emerge in endlessly, and demands from consumers for personal data security raise increasingly. Meanwhile, convenience of operation and diversity of applications are also important for a designer.

In a personal verification system based on security, since a fingerprint identification method may be implemented at a low cost and has the features of high availability and high accuracy, a fingerprint identification device implementing the fingerprint identification method has been widely applied. Currently, the fingerprint identification device is mainly based on a semiconductor silicon capacitance effect, and identifies fingerprint information by using a silicon sensor. In the case of fingerprint identification, a detecting electrode of the silicon sensor is taken as one polar plate of a capacitor, and a finger is taken as the other polar plate of the capacitor. There is a difference in coupling capacitances formed between concave and convex fingerprint textures and a smooth detecting electrode, and difference information of this coupling capacitance is acquired by a terminal, thereby determining concave and convex information of the finger and obtaining fingerprint data of the finger.

However, the fingerprint identification module in the related art needs to be formed separately, and then disposed in the mobile terminal, and there is a relatively high demand on manufacturing and packaging processes, which causes a low production yield and a relatively high cost.

SUMMARY

In a first aspect, at least one embodiment of the present disclosure provides a photosensitive component. The photosensitive component includes: a first electrode layer; a first photosensitive material layer arranged on the first electrode layer; a second electrode layer arranged on the first photosensitive material layer; a second photosensitive material layer arranged on the second electrode layer; and a third electrode layer arranged on the second photosensitive material layer. The first electrode layer is made of an opaque material, and the third electrode layer is made of a transparent material.

In a second aspect, at least one embodiment of the present disclosure provides a display device, including a substrate, on which a plurality of switch elements and a plurality of the above-mentioned photosensitive components are formed. Each of the plurality of switch elements is configured to control the photosensitive component to be turned on or off.

In a third aspect, at least one embodiment of the present disclosure provides a fingerprint identification method, applied to the above-mentioned display device. The method includes:

emitting light to a finger by the display device; and receiving, by the photosensitive component, the light reflected by the finger and forming an illumination current for representing a concave and convex texture of a fingerprint of the finger according to an intensity of the received light.

BRIEF DESCRIPTION OF THE DRAWINGS

In order to more clearly explain the technical solutions of the embodiments of the present disclosure or a related art, the drawings to be used in the descriptions of the embodiments or the related art are briefly introduced as follows. Apparently, the following drawings merely illustrate some embodiments of the present disclosure, and a person skilled in the art can obtain other drawings from these drawings without any creative effort.

DETAILED DESCRIPTION

Figure 1:
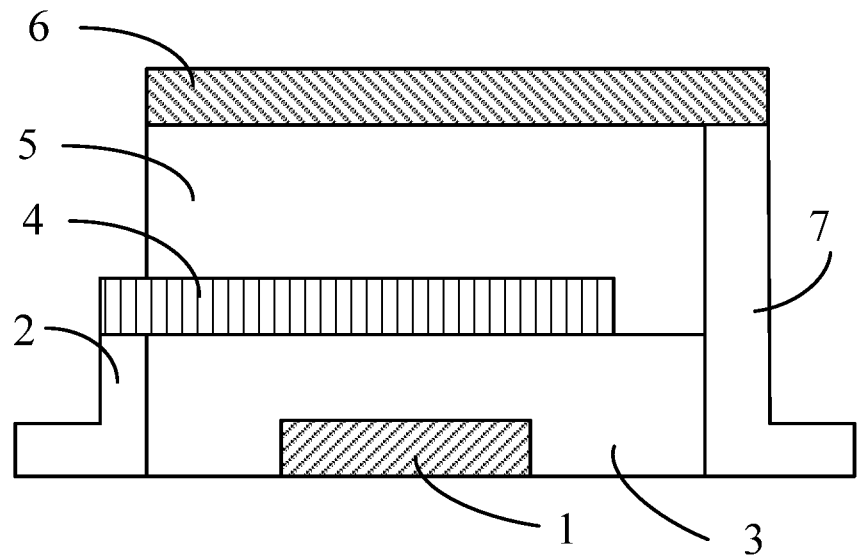
FIG. 1 is a structural schematic diagram of a photosensitive component according to at least one embodiment of the present disclosure.

The present disclosure is further described below in detail in combination with drawings and embodiments. It can be understood that the described embodiments herein are merely used for explaining the related invention, but not to limit the present invention. In addition, it should be further noted that for the sake of convenient description, the parts related to the invention only shown in the drawings.

It should be noted that the embodiments and the features in the embodiments can be combined if no conflict is caused. The present disclosure will be described in detail with reference to the accompany drawings and in combination with the embodiments.

In a mobile terminal in the related art, the fingerprint identification module is usually arranged at a position of Home button in the middle of a lower display area. A user may unlock a mobile phone by putting his or her finger on the Home button. Moreover, when the user needs to purchase various applications in an application store, the fingerprint identification method may also be used to make confirmation, instead of entering a password.

The above-mentioned fingerprint identification module is formed alone at the Home button. Such a design requires to manufacture a fingerprint identification panel separately, and to dig a space on the whole panel for disposing the fingerprint identification panel, which not only increases processes, but also damages the whole effect of the panel.

In addition, in the above-mentioned mobile terminal, the fingerprint identification module is to manufacture a fingerprint identification electrode pattern on a fingerprint identification sensor, a semiconductor chip is packaged at a lower layer of the fingerprint identification electrode pattern, and a coating material and a protective layer are applied on an upper layer of the fingerprint identification electrode pattern. The semiconductor chip is configured to implement signal reception and data processing. The coating material on the upper layer is required to not only cover the color of the semiconductor chip, but also have a good conductivity. The protective layer needs to be very thin, so as to meet a requirement of the sensor for a detection distance. Such a structure has relatively high requirements for the manufacturing and packaging processes, which causes a low production yield, and a relatively high cost.

Referring to FIG. 1, at least one embodiment of the present disclosure provides a photosensitive component, including a light-shielding first electrode layer 1, on which a first photosensitive material layer 3 is arranged, a second electrode layer 4 is arranged on the first photosensitive material layer 3, a second photosensitive material layer 5 is arranged on the second electrode layer 4, and a light-transmitting third electrode layer 6 is arranged on the second photosensitive material layer 5.

In practical use, the first electrode layer 1 is taken as a collector, the second electrode layer 4 is taken as a base, and the third electrode layer 6 is taken as an emitter. In some optional embodiments, the first electrode layer 1 may be taken as an emitter, the second electrode layer 4 may be taken as a base, and the third electrode layer 6 may be taken as a collector.

The first electrode layer 1 is configured to shield light, and the third electrode layer 6 is light-transmitting. The light-shielding first electrode layer 1 is configured to prevent light emitted by the display device from irradiating into the photosensitive component directly, and the light-transmitting third electrode layer 6 makes the light emitted by the display device incident in the photosensitive component from the third electrode layer 6 after reflected by the fingerprint, such that the photosensitive component forms an illumination current.

This photosensitive component may, but not limited to, be formed using an evaporation process. The photosensitive component forms a layered vertical structure by the evaporation process. The first photosensitive material layer 3 and a surface of the second electrode layer 4 form a Schottky contact, so do the second photosensitive material layer 5 and the surface of the second electrode layer 4. Since the first photosensitive material layer 3 and the second photosensitive material layer 5 are disposed at two sides of the second electrode layer 4, two back-to-back Schottky structures are formed. The Schottky structure is similar to a PN junction structure, and the two back-to-back Schottky structures form a device with the same characteristics as a thin film transistor. An output current pattern of this thin film transistor presents unsaturated characteristics. Its output current has a big difference in case of illumination and no illumination, and the characteristics of the photosensitive component may be adjusted by changing the thickness of the first photosensitive material layer 3 and the second photosensitive material layer 5. Under a dark condition, the output current of the photosensitive component meets the following condition: $I_{ec}=\beta I_b^{dark}$; and under the lighting condition, the output current of this photosensitive component meets the following condition: $I_{ec}=\beta I_b^{white}+I_L(1+\beta)$; is an amplification factor of the thin film transistor, $I_L$ is a light current generated under the lighting condition, $I_b^{dark}$ is a current of the base under the dark condition, $I_b^{white}$ is a current of the base under the lighting condition, and $I_{ec}$ is an output current of this photosensitive component.

Figure 3:
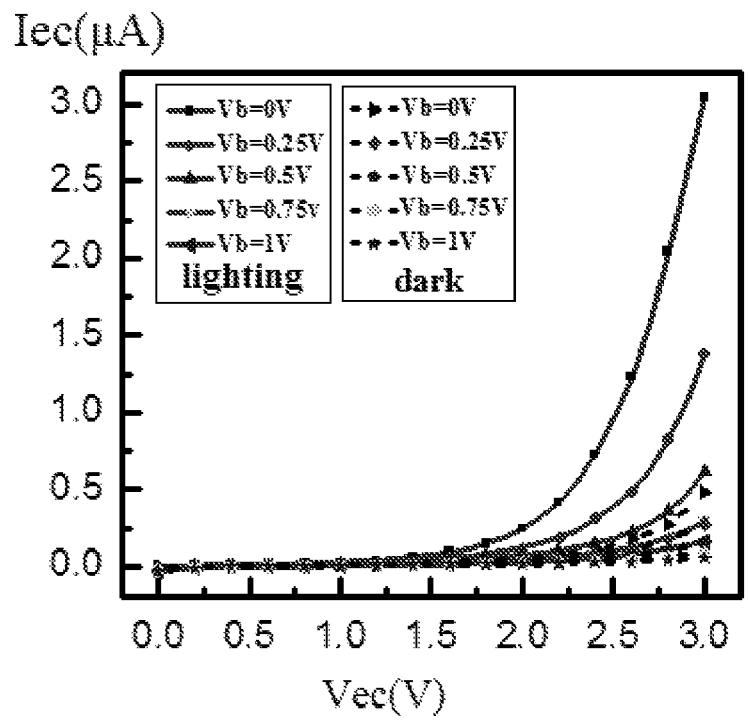
FIG. 3 is a current graph of a photosensitive component under a dark condition and under a lighting condition according to at least one embodiment of the present disclosure.

As shown in FIG. 3, under the lighting and the dark conditions, in the case of the same base voltage $V_b$, and outputting the same voltage $V_{ec}$, the current $I_{ec}$ output under the lighting condition is greater than the current $I_{ec}$ under the dark condition. For example, in the case that $V_{ec}$ is 3V, and $V_b$ is 0V, the current output under the lighting condition is 3 μA, and the current output under the dark condition is about 0.5 μA. As such, the current output under the lighting condition is obviously greater than that input under the dark condition. Such a feature may correspond to the fingerprint identification function. The light rays reflected by convex parts of the fingerprint are more than those reflected by concave parts of the fingerprint. The convex parts of the fingerprint correspond to the current output under the lighting condition, whereas the concave parts of the fingerprint correspond to the current output under the dark condition. Due to the reflection of the concave and convex texture of the fingerprint, there is a different light intensity of the incident light into the photosensitive component corresponding to the concave and convex position of the fingerprint, thereby generating different illumination current, and implementing fingerprint identification according to the difference of output illumination current.

In some optional embodiments, the first photosensitive material layer 3 is connected with the second photosensitive material layer 5. In processing, after the second electrode layer 4 is patterned, a part of the first photosensitive material layer 3 may be exposed outside the second electrode layer 4, and then the second photosensitive material layer 5 is directly formed on the second electrode layer 4. The first photosensitive material layer 3 exposed outside the second electrode layer 4 is connected with the second photosensitive material layer 5. The direct formation of the second photosensitive material layer 5 on the second electrode layer 4 may simplify the process, and the photosensitive component has good electrical properties.

In some optional embodiments, the first photosensitive material layer 3 covers a top surface and a side surface of the first electrode layer 1. In processing, firstly, the first electrode layer 1 is formed on the substrate, and then the first photosensitive material layer 3 is formed to cover the top surface and the side surface of the first electrode layer 1. The first photosensitive material layer 3 is for example, but not limited to be formed by the evaporation process.

In some optional embodiments, a part of the top of the first photosensitive material layer 3 is covered by the second electrode layer 4, and the part not covered by the second electrode layer 4 is connected with the second photosensitive material layer 5. The second electrode layer 4 partially separates the first photosensitive material layer 3 from the second photosensitive material layer 5, and the parts not separated are connected together, so as to form two back-to-back Schottky structures.

In some optional embodiments, the second electrode layer 4 is connected with a first connection line 2 very close to the side surface of the first photosensitive material layer 3; the third electrode layer 6 is connected with a second connection line 7 very close to the side surfaces of the first photosensitive material layer 3 and the second photosensitive material layer 5. As shown in FIG. 1, the first connection line 2 and the second connection line 7 are located on different side surfaces of the first photosensitive material layer 3, which avoids interferences between the first connection line 2 and the second connection line 7. The first connection line 2 and the second connection line 7 are respectively configured to connect the second electrode layer 4 and the third electrode layer 6 to the corresponding function circuit, so as to make the photosensitive component generate and output a photosensitive current. Therefore, a circuit output line of the photosensitive component may be located below or at the side surface of the photosensitive component. By the first connection line 2 and the second connection line 7, the photosensitive component is connected with its circuit output line. In this manner, the top of the photosensitive component may be configured to package the protective layer, and to protect the output line of the photosensitive component, which also eliminates the formation of an additional electrode layer on the top of the photosensitive component, so as to implement the circuit connection of the photosensitive component, simplifies the manufacture process, and lowers costs.

In the embodiments shown in FIG. 1, the second electrode layer 4 is covered on the first connection line 2, and the third electrode layer 6 is covered on the second connection line 7.

Figure 2:
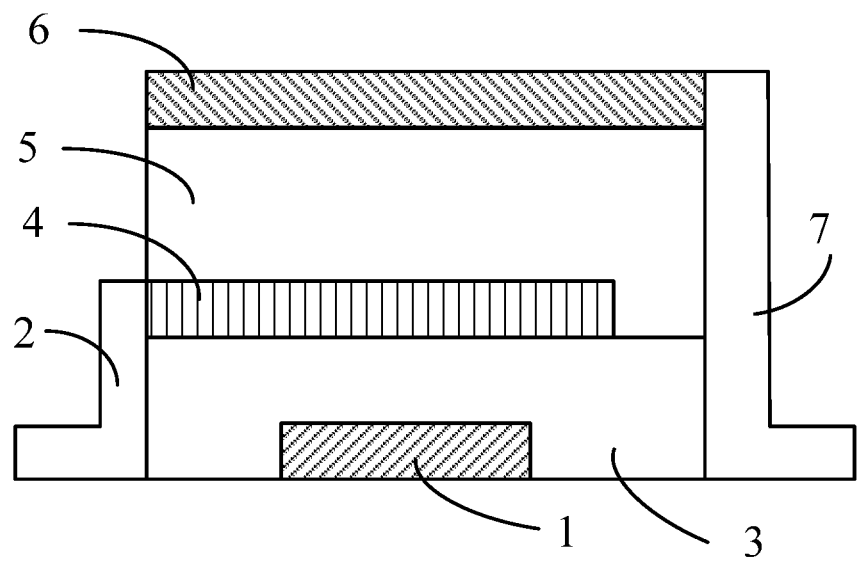
FIG. 2 is a structural schematic diagram of a photosensitive component according to at least one embodiment of the present disclosure.

In some optional embodiments, the first connection line 2 may also be in a close contact with the side surface of the second electrode layer 4, and the second connection line 7 may also be in a close contact with the third electrode layer 6, as shown in FIG. 2.

In actual operations, for the photosensitive components as shown in FIGS. 1 and 2, the first connection line 2 and the second electrode layer 4 may be made of the same material or the same material layer, and formed through a single patterning process. In some optional embodiments, the third electrode layer 6 and the second connection line 7 may also be made of the same material or the same material layer, and formed through a single patterning process. Therefore, the patterning process may be simplified.

In some optional embodiments in FIG. 2, each of the first photosensitive material layer 3 and the second photosensitive material layer 5 is made of organic material.

In some optional embodiments, the first photosensitive material layer 3 and the second photosensitive material layer 5 are both made of CuPc. CuPc is copper phthalocyanine, with a molecular formula of $C_{32}H_{16}N_8Cu$.

In some optional embodiments, the first electrode layer 1 is made of copper, the second electrode layer 4 is made of aluminum, and the third electrode layer 6 is made of gold or ITO (Indium Tin Oxide). The gold film and ITO are both light-transmissive.

The embodiments of the present disclosure further provide a display device, including a substrate, on which a switch element VT1 and the above-mentioned photosensitive component VT2 are formed, and the switch element VT1 configured to control the ON and OFF of the photosensitive component VT2.

As for the switch element VT1, for example, but not limited to, a TFT switch tube may be used.

The display panel may be any product or part with a display function, such as an OLED panel, a mobile phone, a tablet PC, a TV, a display, a note book, a digital photo frame, a navigator, or the like.

In the present technical solution, the photosensitive component is directly formed on the substrate of the display device, without separately manufacturing the fingerprint identification module. The formed display panel directly has a fingerprint identification function. In the production process, this solution reduces the requirement for the process, and increases the production yield. In use, by the OLED (Organic Light Emitting Diode) corresponding to the pixel emitting light to the finger on the panel, and reflecting by the finger to the surface of the photosensitive component, the photosensitive component generates different amplified light current outputs according to different brightness. Such a character just corresponds to the fingerprint identification function. The light rays reflected by convex parts of the fingerprint are more than those reflected by concave parts of the fingerprint. The convex parts of the fingerprint correspond to the current output under the lighting condition, whereas the concave parts of the fingerprint correspond to the current output under the dark condition. Due to the reflection of the concave and convex texture of the fingerprint, there is a different light intensity of the incident light into the photosensitive component corresponding to the concave and convex position of the fingerprint, thereby generating different illumination current, and implementing fingerprint identification according to the difference of output illumination current.

Figure 4:
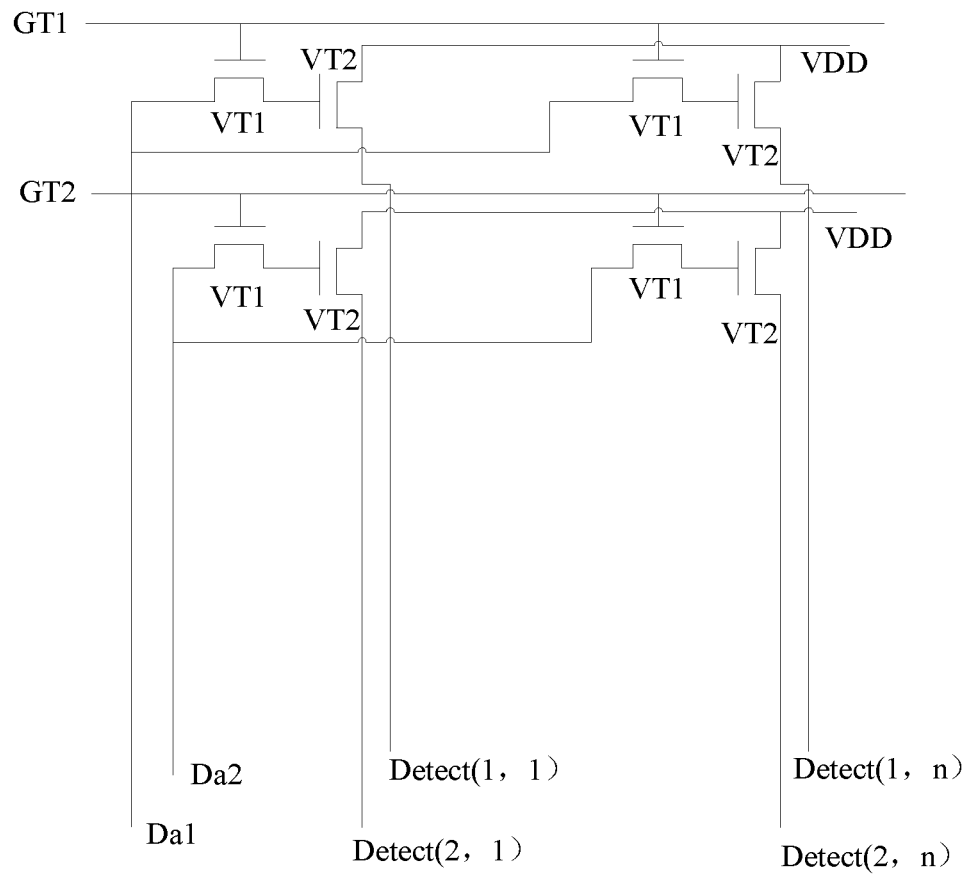
FIG. 4 is a circuit diagram of a display device according to at least one embodiment of the present disclosure.

FIG. 4 is a circuit schematic diagram of the display device, which only shows a circuit connection diagram of 2×n photosensitive components VT2 in the display device. The emitter of the TFT switch tube VT1 is connected with the base of the photosensitive component VT2, the collector of the photosensitive component VT2 is connected with a power voltage VDD, and the emitter of the photosensitive component VT2 is configured to output the resulting light current. The photosensitive components VT2 are arranged in an array in the display, corresponding to the pixel position, which may be located above the pixels, or above a gap between two adjacent pixels correspondingly. By identifying Detect(m, n) as an output of the photosensitive component VT2, outputs of the first row of photosensitive components VT2 are identified as Detect(1, 1) . . . Detect(1, n) respectively, and outputs of the second row of photosensitive components VT2 are identified as Detect(2, 1) . . . Detect(2, n) respectively. The concave and convex texture of the fingerprint at this photosensitive component VT2 may be determined according to a size of an output current of each photosensitive component VT2. The base of the TFT switch tube VT1 is connected with a scanning signal Da. A scanning signal of the first row of TFT switch tubes VT1 is identified as Da1, a scanning signal of the second row of TFT switch tubes VT1 is identified as Da2, and the like. The collector of the TFT switch tube VT1 is connected with a power signal GT. A power signal of the first row of TFT switch tubes VT1 is identified as GT1, a power signal of the second row of TFT switch tubes VT1 is identified as GT2, and the like.

For example, the scanning signal of the TFT switch tube VT1 is provided by a GOA (Gate Driver On Array) circuit integrated on a back plate of the display, and a GOA signal in the back plate is connected to the TFT switch tube VT1. Usually, the photosensitive component is packaged at the outermost layer of the whole display device, and the GOA signal in the back plate is connected to the photosensitive component by punching upwards and passing through each layer on the back plate. In view of a relatively large thickness of the whole display device, in order to improve contact of the circuit, several metal layers or ITO layers may be arranged between photosensitive components of the back plate for transfer. The scanning signal Da scans line by line, and is synchronous with the GT signal. The emitter of the photosensitive component VT2 which is turned on emits a photosensitive current, for determining the concave and convex shapes of the fingerprint. Certainly, other forms of scanning signals may also be utilized, and the TFT switch tube VT1 of each row may be scanned at the same time. The scan mentioned herein refers to press the base of the TFT switch tube VT1, such that the TFT switch tube is turned on.

The ON and OFF of the photosensitive component VT2 is controlled by the TFT switch tube VT1, with advantages of a simple structure, easy implementation, and reduced light-shielding area.

In some optional embodiments, the substrate is flexible. The photosensitive component is formed on the flexible substrate by the evaporation process. For example, the photosensitive component is formed on the flexible TFE (thin film encapsulation) layer by the evaporation process. The evaporation process for forming the photosensitive component may be in good agreement with the flexible TFE substrate process, ensuring the product integrity.

In some optional embodiments, a pixel layer is arranged on the substrate, the photosensitive component is arranged above the pixel of the pixel layer, or the photosensitive component is arranged above the gap between the two adjacent pixels in the pixel layer. In practical use, one photosensitive component may be manufactured above each pixel, and the photosensitive components arranged in an n×m matrix are formed in the display. Since the first electrode layer of the photosensitive component has light-shielding property, the light emitted from the OLED corresponding to the pixel may be prevented from directly being incident in the photosensitive component. However, the photosensitive component is much less than the pixel, so its function of shielding the light emitted from the OLED corresponding to the pixel may be ignored. The light emitted from the OLED is irradiated on the finger of the panel, and then reflected to the upper surface of the photosensitive component by the finger. The photosensitive component generates and outputs different amplified illumination current according to different brightness. This character just corresponds to the fingerprint identification function. The light rays reflected by convex parts of the fingerprint are more than those reflected by concave parts of the fingerprint. The convex parts of the fingerprint correspond to the current output under the lighting condition, whereas the concave parts of the fingerprint correspond to the current output under the dark condition. Due to the reflection of the concave and convex texture of the fingerprint, there is a different light intensity of the incident light into the photosensitive component corresponding to the concave and convex position of the fingerprint, thereby generating different illumination current, and implementing fingerprint identification according to the difference of output illumination current.

Although the photosensitive component is much less than the pixel, the light-shielding first electrode layer may shield less emergent light. Generally, the shielding of the photosensitive component to the light emitted from the OLED is not taken into account, but in the case of requiring the output current with a high accuracy, it needs to improve the shielding of the photosensitive component to the incident light. In some optional embodiments, the photosensitive component may be arranged above the gap between two adjacent pixels in the pixel layer, so as to prevent the photosensitive component from shielding the light emitted from the OLED, and improve the utilization rate of the light rays.

The embodiments of the present disclosure further provide a fingerprint identification method of the above-mentioned display device, including:

emitting light to a finger by the display device; and receiving, by the photosensitive component, the light reflected by the finger and forming an illumination current for representing a concave and convex texture of a fingerprint of the finger according to an intensity of the received light.

In some optional embodiments, the fingerprint determining module forms a fingerprint image according to the intensity of the illumination current.

By the OLED corresponding to the pixel emitting light to the finger on the panel, and then reflecting by the finger to the surface of the photosensitive component, the photosensitive component generates different amplified light current outputs according to different brightness. The higher the illumination intensity, the greater the current. The light reflected by the convex parts of the fingerprint has a high intensity, and the light reflected by the concave parts of the fingerprint has a low intensity. A fingerprint determination module forms the part with a high current intensity as a convex pattern, and forms the part with a low intensity as a concave pattern according to the intensity of the illumination current, so as to reflect the image of fingerprint on the panel.

The above descriptions are merely optional embodiments of the present disclosure, it should be noted that several improvements and modifications may be made for a person skilled in the art without departing from the principle of the present disclosure, and also should be considered to fall within the protection scope of the present disclosure.

What is claimed is:

1. A photosensitive component, comprising:
   a first electrode layer;
   a first photosensitive material layer arranged on the first electrode layer;
   a second electrode layer arranged on the first photosensitive material layer;
   a second photosensitive material layer arranged on the second electrode layer; and
   a third electrode layer arranged on the second photosensitive material layer,
   wherein the first electrode layer is made of an opaque material, and the third electrode layer is made of a transparent material,
   wherein the first photosensitive material layer is connected with the second photosensitive material layer,
   wherein a top portion of the first photosensitive material layer comprises a first part and a second part, wherein the first part is covered by the second electrode layer, and the second part is not covered by the second electrode layer, and is connected with the second photosensitive material layer,
   wherein the photosensitive component further comprises:
   a first connection line arranged in close contact with a first side surface of the first photosensitive material layer, and a second connection line arranged in close contact with a second side surface of the second photosensitive material layer, and
   wherein the second electrode layer is connected with the first connection line, and the third electrode layer is connected with the second connection line.

2. The photosensitive component according to claim 1, wherein the first photosensitive material layer covers a top surface and a side surface of the first electrode Layer.

3. The photosensitive component according to claim 1, wherein the first photosensitive material layer and the second electrode layer form a first Schottky structure, the second photosensitive material layer and the second electrode layer form a second Schottky structure, and the back-to-back first Schottky structure and the second Schottky structure form a thin film transistor.

4. The photosensitive component according to claim 3, wherein an output current of the photosensitive component increases with an increase in an intensity of light incident on a surface of the photosensitive component.

5. The photosensitive component according to claim 1, wherein each of the first photosensitive material layer and the second photosensitive material layer is made of an organic material.

6. The photosensitive component according to claim 5, wherein the first photosensitive material layer and the second photosensitive material layer are each made of CuPc.

7. The photosensitive component according to claim 1, wherein the first electrode layer is made of copper, the second electrode layer is made of aluminum, and the third electrode layer is made of gold or ITO (Indium Tin Oxide).

8. A display device, comprising a substrate, a plurality of switch elements and a plurality of photosensitive components that are formed on the substrate, wherein each of the plurality of switch elements is configured to control the photosensitive component to be turned on or off,
wherein each of the plurality of switch elements comprises a first electrode layer, a first photosensitive material layer arranged on the first electrode layer, a second electrode layer arranged on the first photosensitive material layer, a second photosensitive material layer arranged on the second electrode layer, and a third electrode layer arranged on the second photosensitive material layer, wherein the first electrode layer is made of an opaque material, and the third electrode layer is made of a transparent material,
wherein the first photosensitive material layer is connected with the second photosensitive material layer,
wherein a top portion of the first photosensitive material layer comprises a first part and a second part, wherein the first part is covered by the second electrode layer, and the second part is not covered by the second electrode layer, and is connected with the second photosensitive material layer,
wherein each of the plurality of photosensitive components further comprises a first connection line arranged in close contact with a first side surface of the first photosensitive material layer, and a second connection line arranged in close contact with a second side surface of the second photosensitive material layer, and
wherein the second electrode layer is connected with the first connection line, and the third electrode layer is connected with the second connection line.

9. The display device according to claim 8, wherein the substrate is a flexible substrate.

10. The display device according to claim 8, wherein a pixel layer is arranged on the substrate, each of the plurality of photosensitive components is arranged above pixels of the pixel layer, or each of the plurality of photosensitive components is arranged above a gap between the two adjacent pixels in the pixel layer.

11. The display device according to claim 8, wherein the first photosensitive material layer covers a top surface and a side surface of the first electrode layer.

12. The display device according to claim 8, wherein the first photosensitive material layer and the second photosensitive material layer are each made of CuPc, the first electrode layer is made of copper, the second electrode layer is made of aluminum, and the third electrode layer is made of gold or ITO.

13. A fingerprint identification method, applied to a display device comprising a substrate, a plurality of switch elements and a plurality of photosensitive components that are formed on the substrate, wherein each of the plurality of switch elements is configured to control the photosensitive component to be turned on or off,
wherein each of the plurality of switch elements comprises a first electrode layer, a first photosensitive material layer arranged on the first electrode layer, a second electrode layer arranged on the first photosensitive material layer, a second photosensitive material layer arranged on the second electrode layer, and a third electrode layer arranged on the second photosensitive material layer, wherein the first electrode layer is made of an opaque material, and the third electrode layer is made of a transparent material,
wherein the fingerprint identification method comprises:
emitting light to a finger by the display device; and
receiving, by the photosensitive components, the light reflected by the finger and forming an illumination current for representing a concave and convex texture of a fingerprint of the finger according to an intensity of the received light.

14. The fingerprint identification method according to claim 13, further comprising: forming, by a fingerprint determination module, a fingerprint image according to an intensity of the illumination current.

* * * * *